United States Patent

Voronkov et al.

[11] 4,048,206
[45] Sept. 13, 1977

[54] PROCESS FOR THE PRODUCTION OF 1-ORGANYLSILATRANES AND CARBOFUNCTIONAL DERIVATIVES THEREOF

[76] Inventors: Mikhail Grigorievich Voronkov, ulitsa Lermontova, 315, kv. 32; Valery Mikhailovich Dyakov, ulitsa Lermontova, 263, kv. 23, both of Irkutsk, U.S.S.R.

[21] Appl. No.: 570,493

[22] Filed: Apr. 22, 1975

[51] Int. Cl.$^2$ .................................................. C07F 7/18
[52] U.S. Cl. ............................................. 260/448.8 R
[58] Field of Search .................................. 260/448.8 R

[56] References Cited

U.S. PATENT DOCUMENTS

| | | | |
|---|---|---|---|
| 2,953,545 | 9/1960 | Finestone | 260/448.8 R X |
| 3,118,921 | 1/1964 | Samour | 260/448.8 R |
| 3,133,108 | 5/1964 | Finestone | 260/448.8 R X |
| 3,461,165 | 8/1969 | Frye | 260/448.8 R X |
| 3,560,546 | 2/1971 | Frye | 260/448.8 R |

Primary Examiner—Paul F. Shaver
Attorney, Agent, or Firm—Hasetine, Lake, & Waters

[57] ABSTRACT

A process for the production of 1-organylsilatranes and their carbofunctional derivatives of the general formula X — Z — Si(OR)$_3$N, where R = —CH$_2$—CH$_2$— or —CH(CH$_3$)CH$_2$—; Z is a bivalent hydrocarbon radical; X = H, alkyl, aryl, F, Cl, Br, I, CF$_3$, CN, NH$_2$, SH, CNS, R$^1$M, (R$^2$O)$_2$P(O), R$^3$C(O)M, where R$^1$ is alkyl, aryl, aralkyl or alkaryl; M = O or S; R$^2$ is alkyl; and R$^3$ is alkyl, aryl, R$_F$(a fluorocarbon chain containing from 1 to 10 carbon atoms) or A-C$_6$H$_4$OCH$_2$, where A is halogen, an alkyl group or an alkoxy group which comprises reacting triethanolamine or its derivatives of the general formula

N(ROH)$_3$, where R = —CH$_2$—CH$_2$— or —CH(CH$_3$)CH$_2$—, with 1-organyltrialkoxysilanes of the general formula X — Z — Si(OR$^4$)$_3$, where R$^4$ is alkyl; X = H, alkyl, aryl, I, Br, Cl, F, CF$_3$, CN, NH$_2$, SH, CNS, R$^1$M, (R$^2$O)$_2$P(O) or R$^3$C(O)M, where R$^1$ is alkyl, aryl, aralkyl or alkaryl; M = O or S; R$^2$ is alkyl; and R$^3$ is alkyl, aryl, R$_F$(a fluorocarbon chain containing from 1 to 10 carbon atoms) or A-C$_6$H$_4$OCH$_2$, where A is halogen, an alkyl group or an alkoxy group, in the presence of a low-boiling polar organic solvent or a low-boiling polar organic solvent combined with an alkali catalyst, and subsequently recovering the desired product, and, the triethanolamine or its derivatives are initially admixed with said solvent, after which the 1-organyltrialkoxysilane is added to the reaction mixture.

7 Claims, No Drawings

PROCESS FOR THE PRODUCTION OF 1-ORGANYLSILATRANES AND CARBOFUNCTIONAL DERIVATIVES THEREOF

The present invention is directed to a process for the production of 1-organylsilatranes and their carbofunctional derivatives of the general formula

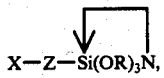
$$X-Z-Si(OR)_3N,$$

where Z is a bivalent hydrocarbon radical; R = $-CH_2CH_2-$ or $-CH(CH_3)CH_2-$; X = H, alkyl, aryl, F, Cl, Br, I, $CF_3$, CN, $NH_2$, SH, CNS, $R^1M$, $(R^2O)_2P(O)$, or $R^3C(O)M$, where $R^1$ is alkyl, aryl, aralkyl or alkaryl; M = O or S; $R^2$ is alkyl; and $R^3$ is alkyl, aryl, $R_F$ (a fluorocarbon chain containing from 1 to 10 carbon atoms) or $A-C_6H_4OCH_2$, where A is halogen, an alkyl group or an alkoxy group. Said compounds find application in medicine for treating wounds, ulcers, burns and dermatitis, as antiallergic drugs for the prevention and treatment of certain forms of baldness, as specific biostimulants in animal husbandry and poultry breeding, as plant growth regulation agents, as additions to synthetic polymers, and also as intermediate products in organic synthesis.

It is known in the art to produce 1-organylsilatranes by ester interchange of appropriate organyltrialkoxysilanes with triethanolamine or its O-methyl-substituted derivatives by the following route:

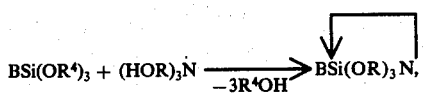
$$BSi(OR^4)_3 + (HOR)_3N \xrightarrow{-3R^4OH} BSi(OR)_3N,$$

where $R^4$ = $CH_3$, or $C_2H_5$; R = $-Ch_2CH_2-$ or $-CH(CH_3)CH_2-$; B = H, F, Cl, $R^5$, $R^5O$ or $D(CH_2)n$, where $R^5$ is alkyl, alkenyl, aryl, alkaryl or aralkyl; D = $NH_2$, CN; and n = 1, 3.

The process is effected in a high-boiling organic solvent (o-dichlorobenzene, o-xylene, methyl ethyl ketone, etc.) or without any solvent, in the presence of a catalyst, e.g. iron chlorides, alkali metal hydroxides, or without any catalyst. The process is conducted with prolonged heating, up to 22 hours, at a temperature of up to 200° C. The shift of the reaction equilibrium to the right achieved by withdrawing the alcohol which is formed in the reaction from the reaction zone. In case an organic solvent is employed, the desired product is recovered by distilling the solvent off and then cooling the reaction mixture. The recovered reaction product is either recrystallized or subjected to multiple extraction with hot heptane (for instance, with B = $R^5O$; $R^5$ is alkyl). The yield of the pure desired product does not exceed 65 percent by weight.

The common disadvantages of the prior art processes consist in the undesirable complexity of the process which involves prolonged heating at high temperatures, entailing partial decomposition of the reaction products, as well as a comparatively low yield of the purified desired product which is due to the multiple recrystallization to cope with the problem of the by-products formed in the reaction.

It is an object of the present invention to raise the yield of the desired product.

It is a further object of the present invention to simplify the process and provide for the production of a highly pure desired product fit for medical applications.

The foregoing objects are attained in a process for the production of 1-organylsilatranes and their carbofunctional derivatives of the general formula

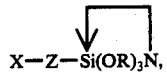
$$X-Z-Si(OR)_3N,$$

where R = $-CH_2CH_2-$ or $-CH(CH_3)CH_2-$; Z is a bivalent hydrocarbon radical; X = H, alkyl, aryl, F, Cl, Br, I, $CF_3$, CN, $NH_2$, SH, CNS, $R^1M$, $(R^2O)_2P(O)$ or $R^3C(O)M$, where $R^1$ is alkyl, aryl, aralkyl or alkaryl; M = O or S; $R^2$ is alkyl; and $R^3$ is alkyl, aryl, $R_F$ (a fluorocarbon chain containing from 1 to 10 carbon atoms) or $A-C_6H_4OCH_2$, where A is halogen, an alkyl group or, an alkoxy group, which comprises reacting triethanolamine or its derivatives of the general formula $$N(ROH)_3,$$

where R = $-CH_2CH_2-$ or $-CH(CH_3)CH_2-$, with 1-organyltrialkoxysilanes of the general formula

$$X-Z-Si(OR^4)_3,$$

where $R^4$ is alkyl; X = H, alkyl, aryl, I, Br, Cl, F, $CF_3$, CN, $NH_2$, SH, CNS, $R^1M$, $(R^2O)_2P(O)$ or $R^3C(O)M$, where $R^1$ is alkyl, aryl, aralkyl or alkaryl; M = O or S; $R^2$ is alkyl; and $R^3$ is alkyl, aryl, $R_F$ (containing from 1 to 10 carbon atoms) or $A-C_6H_4OCH_2$, where A is halogen, an alkyl group or an alkoxy group, in an organic solvent and/or in the presence of a catalyst, and subsequently recovering the desired product, wherein in accordance with the invention, the organic solvent is a low-boiling polar organic solvent, and the process is effected by admixing triethanolamine or its derivatives with the low-boiling polar organic solvent, adding a 1-organyltrialkoxysilane to the reaction mixture, and recovering the desired product. The preferred low-boiling polar organic solvents are acetone, ethanol or methanol.

The process is preferably conducted at a temperature of from 30° to 80° C.

In order to obtain low-melting desired products readily soluble in organic solvents, the process is carried out in the presence of alkali catalysts (alcoholate or hydroxide of an alkali metal) at a temperature of from 40° to 80° C.

The desired product, should it be soluble in the reaction mixture, is preferably recovered by being precipitated from the reaction mixture with the aid of a non-polar low-boiling solvent with cooling to a temperature of from $-70°$ to 0° C, diethyl or petroleum ether, hexane ether, heptane being employed as the non-polar low-boiling organic solvent, or by vacuum distillation.

The process of this invention is carried out by the following route:

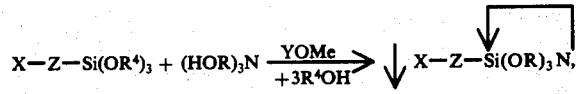
$$X-Z-Si(OR^4)_3 + (HOR)_3N \xrightarrow[+3R^4OH]{YOMe} X-Z-Si(OR)_3N,$$

where R = —CH$_2$CH$_2$— or —CH(CH$_3$)CH$_2$—; Z is a bivalent hydrocarbon radical; R$^4$ = CH$_3$, C$_2$H$_5$; X = H, alkyl, aryl, I, Br, Cl, F, CF$_3$, CN, NH$_2$, SH, CNS, R$^1$M, (R$^2$O)$_2$P(O) or R$^3$C(O)M, where R$^1$ is alkyl, aryl, aralkyl or alkaryl; M = O or S; R$^2$ is alkyl, aryl, R$_F$(a fluorocarbon chain containing from 1 to 10 carbon atoms) or A-C$_6$H$_4$OCH$_2$, where A is halogen, an alkyl group or alkoxy group; Y = H, CH$_3$ or C$_2$H$_5$; Me = K or Na.

Triethanolamine or its derivatives of the general formula

N(ROH)$_3$ where R = —CH$_2$CH$_2$— or —CH(CH$_3$)CH$_2$—, are admixed with 1-organyltrialkoxysilanes of the general formula X — Z — Si(OR$^4$)$_3$, where R$^4$ = CH$_3$ or C$_2$H$_5$; X = H, alkyl, aryl, I, Br, Cl, F, CF$_3$, CN, NH$_2$, SH, CNS, R$^1$M, (R$^2$O)$_2$P(O) or R$^3$C(O)M, where R$^1$ is alkyl, aryl, aralkyl, or alkaryl; M = O or S; R$^2$ is alkyl; and R$^3$ is alkyl, aryl, R$_F$(a fluorocarbon chain containing from 1 to 10 carbon atoms) or A-C$_6$H$_4$OCH$_2$, where A is halogen, an alkyl group or an alkoxy group.

The reaction of said reagents is effected in an organic solvent with or without the presence of a catalyst, the organic solvent being a low-boiling polar organic solvent, such as acetone, ethanol, methanol and the like.

The process is effected by admixing triethanolamine or its derivatives with a low-boiling polar organic solvent, then adding a 1-organyltrialkoxysilane to the reaction mixture, and recovering the desired product. The catalyst (alcoholate or hydroxides of an alkali metal) is optional; however, it facilitates and speeds up the process and sometimes promotes a higher yield of the desired product.

The recovery of th desired product, should it happen to be soluble in the reaction mixture, may be carried out by precipitating it from the reaction mixture with the aid of a non-polar low-boiling solvent with cooling down to a temperature of from −70° to 0° C, petroleum ether, diethyl ether, hexane, heptane and the like being preferably employed as the non-polar low-boiling solvent, or by vacuum distillation. The process is effected at a temperature of from 20° to 100° C, preferably from 30° to 80° C.

The equilibrium shift of the reaction of the proposed process is achieved by removing the desired product from the reaction zone without distilling of the alcohol formed, as often as not in a medium of that same alcohol. The yield of the desired product amounts to 95 percent by weight, and to 85 percent by weight after purification.

The proposed process simplifies the procedure, for the low reaction temperatures employed prevent decomposition of the reaction products and formation of by-products; furthermore, the proposed process yields desired products of a high degree of purity fit for medical applications. The process of this invention permits obtaining 1-organylsilatranes which cannot be synthesized by the prior art techniques what with the inadequate stability or instability of the starting organyltrialkoxysilanes. The yield of the purified desired product is as high as 85 percent by weight, a marked improvement on the prior art yield of the desired product (not more than 65 percent by weight).

In the proposed process, the reagents react practically instantaneously, a feature which significantly adds to the rate of the process, requiring no special apparatus.

Practice of the novel process of this invention for the production of 1-organylsilatranes and their carbofunctional derivatives may be further understood by reference to the following examples.

EXAMPLE 1

A three-necked round-bottomed flask equipped with a reflux condenser, a stirrer and a dropping funnel is charged with 10.8 g (0.07 M) of triethanolamine, 30 ml of absolute ethyl alcohol and 0.2 g of KOH. The solution is heated to boiling and, with intensive stirring, 12.5 g (0.07 M) of (chloromethyl)trimethoxysilane is rapidly poured thereinto, instantly causing the formation of a white crystalline precipitate which is drawn off by suction and dried under vacuum. The yield of 1-(chloromethyl)silatrane with a melting point of 210° to 211° C is 15.5 g (95 wt.%). Upon recrystallization from chloroform, the yield of the pure desired product is 14.6 g (89.wt.%); the product shows a melting point of 220° to 221° C. The product is soluble in chloroform and dimethylformamide (on heating), difficultly soluble in aromatic hydrocarbons, and insoluble in lower alcohols, acetone, CCl$_4$, water and alkanes. From chloroform it is crystallized in the form of transparent cubic crystals; upon reprecipitation with n-hexane, diethyl ether or petroleum ether it is crystallized in the form of a finely divided white crystalline precipitate.

Analysis — Calc'd for C$_7$H$_{14}$O$_{ClNSi}$, wt.%: Si, 12.51; Cl, 15.86; N, 6.26. Found: wt.%: Si, 12.71; Cl, 16.23; N, 6.01.

EXAMPLE 2

An ordinary 50-ml beaker is charged with 10.8 g (0.07 M) of triethanolamine and 12.5 g (0.07 M) of (chloromethyl)trimethoxysilane, after which 2 or 3 drops of a catalyst prepared from 0.5 g of metallic sodium and 20 g of methanol are added to the reaction mixture. As the reaction mixture is agitated with a glass rod, a crystalline precipitate is instantly formed and the temperature of the reaction mixture spontaneously rises from 20° to 45° C. The 1-(chloromethyl)silatrane precipitate is immediately recrystallized from chloroform to yield 13.8 (84.5 wt.%) of a product having a melting point of 220° to 221° C.

EXAMPLE 3

In the apparatus described in Example 1, 24.0 g (0.1 M) of (γ-chloropropyl)trimethoxysilane is rapidly added with intensive stirring to a boiling solution of 15.0 g (0.1 M) of triethanolamine, 0.2 g of KOH and 50 ml of absolute ethanol. Immediately thereafter the reaction mixture is cooled down to a temperature of −20° C., and 10 ml of n-hexane (or diethyl ether) is added thereto. The precipitate is drawn off by suction, washed with ether and dried under vacuum. The yield of 1-(γ-chloropropyl)silatrane having a melting point of 126° to 129° C. is 27.5 g (82.2 wt.%). Upon recrystallization from a mixture of chloroform and heptane, the yield of the pure product having a melting point of 130° to 131° C. is 22.5 g (68.7 wt.%).

Analysis — Calc'd for C$_9$H$_{18}$O$_3$ClNSi, wt.%: Si, 11.12; Cl, 14.08. Found, wt.%: Si, 11.12; Cl, 13.72.

The 1-(γ-chloropropyl)silatrane obtained by the prior art method (with alcohol distillation) has a melting point of 127° to 128° C. and shows a yield of 55.1 wt.%.

EXAMPLE 4

From 10.0 g (methyl)trimethoxysilane, 0.2 g of KOH and 10.9 g of triethanolamine in acetone, by a method similar to that described in Example 1, 11.0 g (79.2 wt.%) of 1-(methyl)-silatrane having a melting point of 142° to 143° C. is obtained.

Analysis — Calc'd for $C_7H_{15}O_3NSi$, wt.%: C, 44.42; H, 7.99; Si, 14.83. Found, wt.%: C, 44.35; H, 7.89; Si, 14.78.

EXAMPLE 5

From 7.5 g (0.05 M) of (dichloromethyl)trimethoxysilane in a methanol solution, by a method similar to that described in Example 1, 10.8 g (83.3 wt.%) of 1-(dichloromethyl)silatrane having a melting point of 255° to 257° C. is obtained. Upon recrystallization from a mixture of chloroform with toluene in the ratio of 4 chloroform to 1 toluene, the product has a melting point of 265° to 268° C.

Analysis — Calc'd for $C_7H_{13}O_3Cl_2NSi$, wt.%: Si, 10.88; Cl, 27.47. Found, wt.% Si, 11.0; Cl, 27.53.

EXAMPLE 6

Duplicating the procedure of Example 1, from 7.5 g of triethanolamine, 0.2 g of KOH and 13.1 g of (iodomethyl)trimethoxysilane in ethanol, 10.5 g (66.6 wt.%) of 1-(iodomethyl)silatrane having a melting point of 182° to 185° C. is obtained.

Upon recrystallization from chloroform, the pure desired product has a melting point of 190° to 191° C.

Analysis — Calc'd for $C_7H_{14}O_3NiSi$, wt.%: Si, 8.90; I, 40.32. Found, wt.%: Si, 9.12; I, 40.91.

EXAMPLE 7

Duplicating the procedure of Example 3, from 11.8 g of triethanolamine, 0.2 g of KOH and 23.2 g of (γ-iodopropyl)-trimethoxysilane (in ethanol), 17.8 g (64.5 wt.%) of 1-(γ-iodopropyl)silatrane having a melting point of 157° to 159° C. is obtained. Upon recrystallization from a mixture of chloroform with chlorobenzene, the yield of the purified desired product is 15.0 g (54.4 wt.%); m.p. 166° to 167° C.

Analysis — Calc'd for $C_9H_{18}O_3NISi$, wt.%: Si, 8.12; I, 36.80. Found, wt.%: Si, 8.61; I, 36.38.

EXAMPLE 8

Duplicating the procedure of Example 1, from 17.9 g of triethanolamine, 0.1 g of KOH and 27.2 g of (α-chloroethane)triethoxysilane, 18.7 g (65.8 wt.%) of 1-(α-chloroethane)silatrane having a melting point of 152° to 153° C. is obtained. The product recrystallized from chloroform has a melting point of 156° to 157° C.

Analysis — Calc'd for $C_8H_{16}O_3ClNSi$, wt.%: Si, 11.81; Cl, 14.96. Found, wt.%: Si, 12.38; Cl, 15.67.

EXAMPLE 9

Duplicating the procedure of Example 1, from 22.0 g of triethanolamine, 0.2 g of KOH and 23.9 g of (β-cyanoethyl) trimethoxysilane, 19.7 g (65.5 wt.%) of 1-(β-cyanoethyl)silatrane having a melting point of 189° to 190° C. is obtained.

Analysis — Calc'd for $C_9H_{16}O_3N_2Si$, wt.%: C, 47.29; H, 7.02; Si, 12.29. Found, wt.%: C, 47.41; H, 7.06; Si, 12.35.

EXAMPLE 10

Duplicating the procedure of Example 1, from 11.2 g (0.075 M) of triethanolamine, 0.1 g of KOH and 16.2 g (0.075 M) of bromomethyl(trimethoxysilane, 16.4 g (81.2 wt.%) of 1-(bromomethyl)silatrane having a melting point of 196° to 198° C. is obtained. Upon recrystallization from chloroform, the product has a melting point of 200° to 201° C.

Analysis — Calc'd for $C_7H_{14}O_3BrNSi$, wt.%: C, 31.34; H, 5.26; Si, 10.47; Br, 29.80. Found, wt.%: C, 31.68; H, 5.43; Si, 10.64; Br, 29.52.

EXAMPLE 11

Duplicating the procedure of Example 1, from 6.28 g (0.042 M) of triethanolamine, 0.1 g of KOH and 12.0 g (0.042 M) of (γ-bromopropyl)triethoxysilane, 10.1 g (69.3 wt.%) of 1-(γ-bromopropyl)silatrane having a melting point of 141° to 143° C. is obtained. Upon recrystallization from chloroform, the product shows a melting point of 147° to 148° C.

Analysis — Calc'd for $C_9H_{18}O_3BrNSi$, wt.%: C, 36.43; H, 6.07; Si, 9.44; Br, 26.97. Found, wt.%: C, 36.08; H, 6.0; Si, 9.45; Br, 27.15.

EXAMPLE 12

Duplicating the procedure of Example 2, from 8.3 g (0.054 M) of triethanolamine and 12.0 g (0.054 M) of (γ-fluoropropyl)triethoxysilane, 12.7 g (96.0 wt.%) of 1-(γ-fluoropropyl) silatrane having a melting point of 66° to 68° C. is obtained. Upon recrystallization from chloroform, the desired product has a melting point of 72° to 72.5° C.

Analysis — Calc'd for $C_9H_{18}O_3NSiF$, wt.%: C, 45.93; H, 7.71; Si, 11.93; F, 8.07. Found, wt.%: C, 45.92; H, 7.70; Si, 11.31; F, 7.73.

EXAMPLE 13

Duplicating the procedure of Example 1, from 10.8 g (0.07 M) of triethanolamine and 18.2 g (0.07 M) of (γ-trifluoropropyl)triethoxysilane, 14.7 g (77.5 wt.%) of 1(γ-trifluoropropyl)silatrane having a melting point of 110° to 111° C. is obtained. Upon recrystallization from chloroform, the product shows a melting point of 108° to 109° C.

Analysis — Calc'd for $C_9H_{16}O_3NSiF_3$, wt.%: C, 39.98; H, 5.94; Si, 10.35; F, 21.0. Found, wt.%: C, 39.63; H, 5.93; Si, 11.18; F, 21.15.

EXAMPLE 14

5.5 g (0.022 M) of (phenylthiomethyl)trimethoxysilane, 3.4 g (0.022 M) of triethanolamine and 0.1 ml of a 3-percent methanol solution of sodium methylate are mixed in a glass beaker, and the reaction mixture is heated to a temperature of 70° C. The alcohol which forms boils, and a white crystalline precipitate is instantly formed; the latter is filtered off, washed with ethanol and ether, and dried. The yield of industrial-grade 1-(phenylthiomethyl)silatrane is 6.5 g (97.0 wt.%); m.p. 241° to 242° C. Upon recrystallization in n-hexane, the yield of the pure desired product (snow-white laminated crystals) having a melting point of 245° to 246° C. is 5.0 g (74.5wt.%).

Analysis — Calc'd for $C_{13}H_{19}O_3NSSi$, wt.%: C, 52.50; H, 6.44; S, 10.76; Si, 9.44. Found, wt.%: C, 52.96; H, 6.36; S, 10.67; Si, 9.17.

EXAMPLE 15

Duplicating the procedure of Example 14, from 8.5 g (0.05 M) of (chloromethyl)trimethoxysilane and 9.6 g (0.05 M) of triisopropanolamine in the presence of 0.1 g of KOH (75° to 85° C.; 15 minutes), 11.7 g (88.0 wt.%) of 1-(chloromethyl-3,7,10÷trimethyl)silatrane having a melting point of 102° to 103° C. is obtained. The pure desired product precipitated from chloroform with the aid of diethyl ether looks like a finely divided white crystalline powder. As distinct from 1-chloromethylsilatrane (Examples 1 and 2), the triisopropanolamine analog is readily soluble in water, lower alcohols, acetone and carbon tetrachloride.

Analysis — Calc'd for $C_{10}H_{20}C_3ClNSi$, wt.%: C, 45.56; H, 7.58; Si, 10.56; Cl, 13.34. Found, wt.%: C, 45.76; H, 7.83; Si, 11.0; Cl, 13.83.

EXAMPLE 16

Duplicating the procedure of Example 2, from 8.5 g (0.05 M) of chloromethyl)trimethoxysilane and 8.9 g (0.05 M) of (diisopropanol)ethanolamine (90° to 100° C.; 40 minutes), 11.8 g (93.4 wt.%) of 1-(chloromethyl-3,7-dimethyl)silatrane having a melting point of 121° to 122° C. is obtained in the form of white needles (n-heptane).

Analysis — Calc'd for $C_9H_{18}O_3ClNSi$, wt.%: C, 42.89; H, 7.21; Si, 11.15; Cl, 14.08. Found, wt.%: C, 43.31; H, 7.20; Si, 11.14; Cl, 13.61.

EXAMPLE 17

Duplicating the procedure of Example 2, from 11.0 g (0.05 M) of ethylthiopropyl)trimethoxysilane and 7.45 g (0.05 M) of triethanolamine, 12.4 g of 1-(ethylthiopropyl)silatrane are obtained (90.0 wt.%) (white needles from n-hexane); m.p. 55° to 56° C.

Analysis — Calc'd for $C_{11}H_{23}O_3NSSi$, wt.%: S, 11.56; Si, 10.12. Found, wt.%: S, 11.61; l Si, 9.71.

EXAMPLE 18

Duplicating the procedure of Example 14, from 7.5 to (0.035 M) of (acetylthiomethyl)trimethoxysilane and 5.3 g (0.035 M) of triethanolamine, 8.5 g (92.2 wt.%) of 1-(acetylthiomethyl)silatrane having a melting point of 204° to 206° C. is obtained. Upon recrystallization from n-hexane, the yield of the product having a melting point of 210° to 211° C. is 7.2 g (78.0 wt.%).

Analysis — Calc'd for $C_9H_{17}O_4NSSi$, wt.%: C, 41.20; H, 6.47; S, 12.15; Si, 10.63. Found, wt.%: C, 41.80; H, 6.50; S, 12.35; Si, 9.16.

EXAMPLE 19

Duplicating the procedure of Example 2, from 16.5 g (0.085 M) of (thiocyanatomethyl)trimethoxysilane and 12.8 g (0.085 M) of triethanolamine, 19.5 g (90.5 wt.%) of industrial grade 1-(thiocyanatomethyl)silatrane having a melting point of 165° to 167° C. is obtained. The product recrystallization from chloroform has a melting point of 170° to 171° C.

Analysis — Calc'd for $C_8H_{14}O_3N_2SSi$, wt.%; C, 39.09; H, 5.74; S, 13.02; Si, 11.43. Found, wt.%: C, 38.91; H, 5.81; S, 12.83; Si, 10.89.

EXAMPLE 20

Duplicating the procedure of Example 2, from 5.0 g (0.033 M) of triethanolamine and 10.0 g (0.033 M) of (o-cresylhydroxyacetylmethyl)trimethoxysilane 9.5 g (80.0 wt.%) of 1-(o-cresylhydroxyacetyl)silatrane having a melting point of 145° to 147° C. is obtained. Upon crecrystallization from chloroform, the product has a melting point of 147.5° to 148.5° C.

Analysis — Calc'd for $C_{16}H_{28}O_6NSi$, wt.%: C, 54.38; H, 6.56; Si, 7.95; N, 3.96. Found, wt.%: C, 54.02; H, 6.45; Si, 7.86; N, 3.75.

EXAMPLE 21

Duplicating the procedure of Example 2, from 7.0 g (0.03 M) of (phenoxymethyl)trimethoxysilane and 4.5 g (0.03 M) of triethanolamine, 6.5 g (75.5 wt.%) of 1-(phenoxymethyl)silatrane having a melting point of 167° to 168° C. is obtained (chloroform; long transparent prisms). Upon reprecipitation with diethyl ether or petroleum ether, the desired product is recovered as a snow-white fine-crystalline powder having a melting point of 168° to 168.5° C.

Analysis — Calc'd for $C_{13}H_{19}O_4NSi$, wt.%: C, 55.50; H, 6.76; Si, 9.95; N, 4.98. Found, wt.%: C, 55.71; H, 7.13; Si, 9.58; N, 4.76.

EXAMPLE 22

Duplicating the procedure of Example 14, from 4.5 g (0.033 M) of triethanolamine and 10.4 g (0.033 M) of (diethylphosphonomethyl)triethoxysilane, 8.3 g (80.0 wt.%) of 1-(0,0-diethylphosphonomethyl)silatrane is obtained in the form of a dark-yellow oil readily soluble in chloroform, ethanol, acetone and acetonitrile. Highvacuum distillation of the industrial-grade product obtained yields 7.4 g (71.3 wt.%) of the pure desired product in the form of a transparent light-yellow oil having a boiling point of 194° to 194.5° C. (0.08 mm Hg; m.p. 72° to 73° C.).

Analysis — Calc'd for $C_{11}H_{24}O_6NPSi$, wt.%: C, 40.61; H, 7.44; P, 9.52; Si, 8.63. Found, wt.%: C, 40.81; H, 7.46; P, 9.01; Sim 8.41

EXAMPLE 23

In a procedure duplicating that of Example 14, from 6.0 g (0.04 M) of triethanolamine and 13.7 g (0.04 M) of (γ-0,0-diethylphosphonopropyl)triethoxysilane, 12.5 g (89.6 wt.%) of industrial-grade 1-(γ-0,0-diethylphosphonopropyl)silatrane is obtained in the form of a darkyellow oil. The latter is dissolved in chloroform and reprecipitated with the aid of diethyl ether with cooling to a temperature of −30° C. The yield of the purified desired product (transparent oil) is 10.8 g (77.5 wt.%). Allowed to stand in a vacuum desiccator, the oil slowly crystallizes; m.p. 50° to 53° C.

High-vacuum distillation of the industrial-grade product yields purified 1-(γ-0,0-diethylphosphonopropyl)silatrane having a boiling point of 175° to 176.5° C. (0.1 mm Hg; m.p. 51° to 52° C.).

Analysis — Calc'd for $C_{13}H_{28}O_6NPSi$, wt.%: C, 44.18; H, 7.94; P, 8.76; Sim 7.95. Found, wt.%: C, 43.88; H, 7.83; P, 9.48; Si, 8.34.

EXAMPLE 24

Duplicating the procedure of Example 14, from 7.4 g (0.049 M) of triethanolamine and 11.0 g (0.049 M) of (γ-amino-propyl)triethoxysilane, 11.7 g (theoretically 11.6 g) of 1-(γ-aminopropyl)silatrane having a melting point of 82° to 85° C. is obtained in the form of a yellow oil rapidly crystallizing upon cooling. Upon recrystalliization or reprecipitation with n-heptane (or n-hexane), the product has a melting point of 87.5° to 88.5° C.

Analysis — Calc'd for $C_9H_{20}O_3N_2Si$, wt.%: N, 12.06; Si, 12.10. Found, wt.%: N, 11.93; Si, 12.70.

EXAMPLE 25

Duplicating the procedure of Example 14, from 10.0 g (0.04 M) of (benzylthiomethyl)trimethoxysilane and 5.8 g (0.04 M) of triethanolamine, 10.5 g (91.0 wt.%) of 1-(benzylthiomethyl)silatrane having a melting point of 147° to 148° C. is obtained. Upon recrystallization from n-heptane, the product has a melting point of 150° to 150.5° C.

Analysis — Calc'd for $C_{14}H_{21}HSSi$, wt.%: C, 54.0; H, 6.79; S, 10.27; Si, 9.02. Found, wt.%: C, 54.01; H, 6.93; S, 10.02; Si, 9.18.

EXAMPLE 26

Duplicating the procedure of Example 14, from 5.8 g (0.032 M) of (β-mercaptoethyl)triethoxysilane and 4.8 g (0.032 M) of triethanolamine, 6.5 g (90.7 wt.%) of 1-(β-mercaptoethyl)silatrane having a melting point of 129° to 130° C. is obtained. Upon recrystallization from chloroform, the yield of the purified desired product in the form of white needles having a melting point of 133° to 134° C. is 5.9 g (82.5 wt.%). Analysis — Calc'd for $C_8H_{17}O_3NSSi$, wt.%: C, 40.80; H, 7.23; S, 13.61; Si, 11.92. Found, wt.%: C, 40.56; H, 7.02; S, 12.92; Si, 11.75.

EXAMPLE 27

Duplicating the procedure of Example 2, from 17.0 g (0.076 M) of (tert-butylthiomethyl)trimethoxysilane and 11.3 g (0.076 M) of triethanolamine, 20.0 g (95.0 wt.%) of 1-(tertbutylthiomethyl)silatrane having a melting point of 194° to 195° C. is obtained. Upon reprecipitation from a chloroform solution with n-hexane, the yield of the pure desired product having a melting point of 201° to 202° C. amounts to 19.2 g (91.3 wt.%).

Analysis — Calc'd for $C_{11}H_{23}O_3NSSi$, wt.%: S, 11.53; Si, 10.12. Found, wt.%: S, 10.84; Si, 9.97.

EXAMPLE 28

Duplicating the procedure of Example 14, from 21.0 g (0.1 M) of (propylthiomethyl)trimethoxysilane and 14.9 g (0.1 M) of triethanolamine, 25.0 g (95.0 wt.%) of 1-(propylthiomethyl)silatrane having a melting point of 147° to 148° C. is obtained. The product recrystallized from n-heptane in the form of colorless long needles has a melting point of 150° to 150.5° C.

Analysis — Calc'd for $C_{10}H_{21}O_3NSSi$, wt.%: S, 12.18; Si, 10.67. Found, wt.%: S, 12.10; Si, 10.77.

EXAMPLE 29

Duplicating the procedure of Exakmple 14, from 10.0 g (0.025 M) of β-(phenylthioethyl)triethoxysilane and 3.6 g (0.025 M) of triethanolamine (in the presence of 0.05 g of KOH), 7.1 g (93.1 wt.%) of 1-(β-phenylthioethyl)silatrane having a melting point of 109° to 111° C. is obtained. The product recrystallized from n-hexane has a melting point of 112° to 112.5°.

Analysis — Calc'd for $C_{14}H_{21}O_3NSSi$, wt.%: S, 10.27; Si, 9.02. Found, wt.%: S, 10.15; Si, 8.87.

EXAMPLE 30

Duplicating the procedure of Example 2, from 7.2 g (0.026 M) of (γ-ortho-cresylhydroxypropyl)trimethoxysilane and 3.9 g (0.026 M) of triethanolamine, 8.0 g (93.0 wt.%) of 1-(γ-orthocresylhydroxypropyl)silatrane having a melting point of 102° to 103° C. is obtained. The purified product (n-hexane; snow-white needles) has a melting point of 105° to 106° C.

Analysis — Calc'd for $C_{16}H_{25}O_4NSi$, wt.%: C, 69.43; H, 7.79; N, 4.33; Si, 8.68. Found, wt.%: C, 60.19; H, 8.18; N, 5.65; Si, 8.51.

EXAMPLE 31

Duplicating the procedure of Example 2, from 5.2 g (0.017 M) of (ortho-methoxyphenoxymethyl)triethoxysilane and 2.6 g (0.017 M) of triethanolamine, 5.1 g (95.0 wt.%) of 1-(ortho-methoxyphenoxymethyl) silatrane is obtained which, after recrystallization from n-hexane, has a melting point of 142° to 143° C.

Analysis — Calc'd for $C_{14}H_{21}O_5NSi$, wt.%: C, 53.85; H, 6.75; N, 51; Si, 8.96. Found, wt.%: C, 53.99; H, 6.67; N, 4.57; Si, 8.51.

EXAMPLE 32

Duplicating the procedure of Example 2, from 10.0 g (0.028 M) of (p-iodophenoxymethyl)trimethoxysilane and 4.2 g (0.028 M) of triethanolamine, 10,0 g (87.0 wt.%) of 1-(p-iodophenoxymethyl)silatrane having a melting point of 187° to 188° C. is obtained. The product is obtained after reprecipitation from a chloroform solution with diethyl ether in the form of a fine-crystalline white powder.

Analysis — Calc'd for $C_{13}H_{18}O_4NI\ Si$, wt.%: I, 31.17; Si, 6.87. Found, wt.%: I, 30.92; Si, 6.28.

What is claimed is:

1. A process for the production of a 1-organylsilatrane of the formula

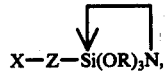

where R is selected from the group consisting of —CH$_2$—CH$_2$— and —CH(CH$_3$)CH$_2$—; Z is a bivalent hydrocarbon radical; X is selected from the group consisting of H, alkyl, aryl, F, Cl, Br, I, CF$_3$, CN, NH$_2$, SH, CNS, R$^1$M, (R$^2$O)$_2$P(O) and R$^3$C(O)M, where R$^1$ is selected from the group consisting of alkyl, aryl, aralkyl or alkaryl; M is selected from the group consisting of O and S; R$^2$ is alkyl; and R$^3$ is selected from the group consisting of alkyl, aryl, R$_F$ and A-C$_6$H$_4$OCH$_2$, where R$_F$ is a fluorocarbon chain containing from 1 to 10 carbon atoms and A is selected from the group consisting of halogen, an alkyl group and an alkoxy group, which comprises reacting an amine of the formula

where R is selected from the group consisting of —CH$_2$—CH$_2$— and —CH(CH$_3$)CH$_2$—, with a 1-organyltrialkoxysilane of the formula

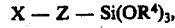

where R$^4$ is alkyl; X is selected from the group consisting of H, alkyl, aryl, I, Br, Cl, F, CF$_3$, CN, NH$_2$, SH, CNS R$^1$M, (R$^2$O)$_2$P(O) and R$^3$C(O)M, where R$^1$ is selected from the group consisting of alkyl, aryl, aralkyl and alkaryl; M is selected from the group consisting of O and S; R$^2$ is alkyl; and R$^3$ is selected from the group consisting of alkyl, aryl, R$_F$ and A-C$_6$H$_4$OCH$_2$, where R$_F$ is a fluorocarbon chain containing from 1 to 10 carbon atoms and A is selected from the group consisting of halogen, an alkyl group and an alkoxy group, in the presence of a low-boiling polar organic solvent at 20° to 100° C. and subsequently recovering the desired product, and the amine is initially admixed with said solvent, after which the 1-organyltrialkoxysilane is added to the reaction mixture.

2. The process of claim 1, wherein the low-boiling polar organic solvent is selected from the group consisting of acetone, ethanol and methanol.

3. The process of claim 1, wherein the process temperature lies in the range from 30° to 80° C.

4. The process of claim 1, wherein the recovery of the desired product, should the latter be soluble in the reaction mixture, is carried out by precipitating the desired product from the reaction mixture with the aid of a non-polar low-boiling solvent with cooling to a temperature of from −70° to 0° C.

5. The process of claim 4, wherein the non-polar low-boiling organic solvent is selected from the group consisting of diethyl ether, petroleum ether, hexane and heptane.

6. The process of claim 1 wherein the process is carried out in the presence of an alkali catalyst.

7. The process of claim 6 wherein the low-boiling polar organic solvent is selected from the group consisting of acetone, ethanol and methanol.

* * * * *